(12) United States Patent
Kirchhofer et al.

(10) Patent No.: US 6,699,224 B2
(45) Date of Patent: Mar. 2, 2004

(54) DEVICE FOR ADMINISTERING AN INJECTABLE PRODUCT

(75) Inventors: Fritz Kirchhofer, Sumiswald (CH); Thomas Gurtner, Koppigen (CH)

(73) Assignee: Disetronic Licensing AG, Burgdorf (CH)

( * ) Notice: Subject to any disclaimer, the term of this patent is extended or adjusted under 35 U.S.C. 154(b) by 265 days.

(21) Appl. No.: 09/903,152

(22) Filed: Jul. 11, 2001

(65) Prior Publication Data

US 2002/0016571 A1 Feb. 7, 2002

Related U.S. Application Data

(63) Continuation of application No. PCT/CH00/00017, filed on Jan. 11, 2000.

(30) Foreign Application Priority Data

Jan. 12, 1999 (DE) .......................... 199 00 792

(51) Int. Cl.⁷ ................................ A61M 5/00
(52) U.S. Cl. .................... 604/208; 604/209; 604/211
(58) Field of Search ....................... 604/93.01, 131, 604/134, 135, 187, 207, 208, 209, 210, 211, 218, 224

(56) References Cited

U.S. PATENT DOCUMENTS

| | | | |
|---|---|---|---|
| 2,695,023 A | 11/1954 | Brown | 128/218 |
| 3,605,744 A | 9/1971 | Dwyer | 128/218 F |
| 4,082,121 A | 4/1978 | Sturm et al. | 141/27 |
| 4,313,439 A | 2/1982 | Babb et al. | 128/214 F |
| 4,552,561 A | 11/1985 | Eckenhoff et al. | 604/869 |
| 4,592,745 A | 6/1986 | Rex et al. | 604/211 |
| 4,659,327 A | 4/1987 | Bennett et al. | 604/135 |
| 4,735,611 A | 4/1988 | Anderson et al. | 604/130 |
| 4,813,870 A | 3/1989 | Pitzen et al. | 433/90 |
| 4,865,591 A | 9/1989 | Sams | 604/186 |
| 4,883,472 A | 11/1989 | Michel | 604/208 |

(List continued on next page.)

FOREIGN PATENT DOCUMENTS

| | | | |
|---|---|---|---|
| CA | 2 155 575 | 7/1999 | A61M/5/315 |
| DE | 2 056 688 | 3/1972 | A61M/5/28 |
| DE | 19519147 A1 | 12/1995 | A61M/5/20 |
| EP | 0 265 214 | 4/1988 | A61K/37/26 |
| EP | 0 279 583 A2 | 8/1988 | A61M/5/34 |

(List continued on next page.)

OTHER PUBLICATIONS

Cutler, Paul, "Deferoxamine Therapy in High–Ferritin Diabetes", Journal of American Diabetes Associateion, vol. 38, No. 10, (5pgs) (Oct. 1989).

Primary Examiner—Manuel Mendez
Assistant Examiner—Mark K Han
(74) Attorney, Agent, or Firm—Dorsey & Whitney LLP

(57) ABSTRACT

The invention refers to a device for administering an injectable product in doses, comprising a casing, itself comprising: a reservoir for the product; a piston which forces product out of the reservoir when moved in a feed direction towards a reservoir outlet; a drive member; a driven member which is slaved by the drive member when the drive member is moved in the feed direction, so moving the piston in the feed direction; and a dosing member which may be rotated about the sliding axis of the drive member, to set the product dosage to be administered. The drive member and the dosing member abut each other via at least one dosage stopper each, one of which is provided on the drive member and the other on the dosing member. At least one of these dosage stoppers at least partially encircles the sliding axis of the drive member in the form of a spiral. The at least one spiral dosage stopper exhibits a continuous course with a constant pitch $\alpha$.

17 Claims, 2 Drawing Sheets

U.S. PATENT DOCUMENTS

| | | | |
|---|---|---|---|
| 4,894,054 A | 1/1990 | Miskinyar | 604/136 |
| 4,936,833 A | 6/1990 | Sams | 604/232 |
| 4,946,446 A | 8/1990 | Vadher | 604/198 |
| 4,973,318 A | 11/1990 | Holm et al. | 604/208 |
| 5,015,235 A | 5/1991 | Crossman | 604/117 |
| 5,017,190 A | 5/1991 | Simon et al. | 604/207 |
| 5,059,181 A | 10/1991 | Agran | 604/110 |
| 5,114,406 A | 5/1992 | Gabriel et al. | 604/136 |
| 5,244,465 A | 9/1993 | Michel | 604/208 |
| 5,273,544 A | 12/1993 | van der Wal | 604/134 |
| 5,279,585 A | 1/1994 | Balkwill | 604/207 |
| 5,279,586 A | 1/1994 | Balkwill | 604/207 |
| 5,304,152 A | 4/1994 | Sams | 604/207 |
| 5,337,756 A | 8/1994 | Barbier et al. | 128/763 |
| 5,480,387 A | 1/1996 | Gabriel et al. | 604/134 |
| 5,496,293 A | 3/1996 | Huggenberger | 604/208 |
| 5,514,097 A | 5/1996 | Knauer | 604/136 |
| 5,549,558 A | 8/1996 | Martin | 604/110 |
| 5,584,815 A | 12/1996 | Pawelka et al. | 604/191 |
| 5,599,323 A | 2/1997 | Bonnichsen et al. | 604/272 |
| 5,611,783 A | 3/1997 | Mikkelsen | 604/208 |
| 5,626,566 A | 5/1997 | Petersen et al. | 604/208 |
| 5,634,903 A | 6/1997 | Kurose et al. | 604/110 |
| 5,643,214 A | 7/1997 | Marshall et al. | 604/134 |
| 5,679,111 A | 10/1997 | Hjertman et al. | 604/135 |
| 5,807,346 A | 9/1998 | Frezza | 604/208 |
| 5,984,900 A | 11/1999 | Mikkelsen | 604/208 |
| 6,042,571 A | 3/2000 | Hjertman et al. | 604/208 |
| 6,086,567 A | 7/2000 | Kirchhofer et al. | 604/211 |
| 6,241,709 B1 | 6/2001 | Bechtold et al. | 604/207 |

FOREIGN PATENT DOCUMENTS

| | | | | |
|---|---|---|---|---|
| EP | 0 295 075 A1 | 12/1988 | | A61M/5/315 |
| EP | 0 498 737 A1 | 8/1992 | | A61M/5/315 |
| JP | 4-256757 | 9/1992 | | A61M/5/315 |
| JP | 4-256758 | 9/1992 | | A61M/5/315 |
| JP | 5-161713 | 6/1993 | | A61M/5/315 |
| WO | WO 91/10460 | 7/1991 | | A61M/5/24 |
| WO | WO 93/16740 | 9/1993 | | |
| WO | WO 94/17846 | 8/1994 | | A61M/5/315 |
| WO | WO 94/26331 | 11/1994 | | A61M/5/20 |
| WO | WO 96/07443 | 3/1996 | | A61M/5/315 |
| WO | WO 97/30742 | 8/1997 | | A61M/5/178 |
| WO | WO 00/41753 | 7/2000 | | A61M/5/315 |

DEVICE FOR ADMINISTERING AN INJECTABLE PRODUCT

This U.S. patent application Ser. No. 09/903,152, filed Jul. 11, 2001, claims priority to and is a continuation application of PCT application PCT/CH 00/00017, filed Jan. 11, 2000, which claims priority to German patent application DE 19900792.6, filed Jan. 12, 1999 and issuing Jun. 15, 2000 as German Patent DE 199 00 792 Cl.

BACKGROUND OF THE INVENTION

1. Field of the Invention

The invention relates to a device for administering an injectable product, as set forth in the preamble of claim 1.

2. Description of Related Art

An injection device, such as the invention also relates to, is known from WO 97/36625. The injection device comprises: a casing; a product reservoir with a piston movably accommodated therein, which when moved in a feed direction forces product out of the reservoir; a drive means; and a dosing means.

The drive means comprises a drive member which can be moved along a sliding axis up to a proximal end position in the feed direction and up to a distal end position counter to the feed direction, and a driven member which is prevented from moving counter to the feed direction, but which is slaved by the drive member when the drive member is moved in the feed direction, so moving the piston in the feed direction such that product is forced out of the reservoir. When setting the path length which the driven member covers in one complete stroke, and thus the product dosage to be delivered, the drive member is moved counter to the feed direction and relative to the driven member back to its distal end position. The distal end position is set by means of a dosing means, while the proximal end position is defined by a stopper on the casing.

The dosing means comprises the drive member and the dosing member for setting the distal end position of the drive member. The dosing member is positioned in the casing and may be rotated about the sliding axis of the drive member. It comprises a dosage stopper encircling the sliding axis in the form of a spiral, which the drive member abuts if moved to the distal position, i.e. the distal position of the drive member is determined by the rotational angular position of the dosing member.

The product dosage to be delivered is selected by rotating the dosing member in discrete steps. For this purpose, the dosing member locks in rotational angular locking positions provided at regular intervals between the casing and the dosing member. Rotating the dosing member between two adjacent blocking positions corresponds to the smallest adjustable product dosage. The spirally encircling dosage stopper of the dosing member exhibits a discontinuous course. It drops in discrete steps from a most proximal section to its most distal section. A dosage cam radially projecting from the drive member is provided thereon as a dosage counter stopper which, when the drive member is moved back for dosing, is moved up against the section of the dosage stopper of the dosing member which lies opposite the cam due to the rotation of the dosing member. The dosage cam of the drive member is very slim in this construction.

SUMMARY OF THE INVENTION

It is an object of the invention to provide a device, particularly of the above kind, for administering an injectable product, said device exhibiting a high mechanical strength as regards the components used for product dosage, wherein the dosage precision and accuracy of previously known devices is at least maintained.

The invention concerns a device for the dosed administering of an injectable product, comprising:

a) a casing, comprising a reservoir for the product;
b) a piston, forcing product out of the reservoir when moved in a feed direction towards a reservoir outlet;
c) a drive member, which may be moved along a sliding axis in the feed direction up to a proximal end position, and against the feed direction up to a distal end position;
d) a driven member, which is prevented from moving against the feed direction, and is slaved by the drive member when the drive member is moved in the feed direction, so moving the piston in the feed direction;
e) a dosing member, which may be rotated about the sliding axis of the drive member, to set the product dosage to be administered;
f) wherein in the distal end position, the drive member and the dosing member abut via at least one dosage stopper each, one of which is provided on the drive member and the other on the dosing member, the drive member and the dosing member preferably abutting each other via said stoppers; and wherein
g) at least one of these dosage stoppers at least partially encircles the sliding axis of the drive member in the form of a spiral.

According to the invention, said at least one spiral dosage stopper exhibits a continuous course and a constant pitch relative to the sliding axis of the drive member.

Although the spiral dosage stopper does not essentially have to entirely encircle the sliding axis, a spiral dosage stopper which does is preferred. The spiral dosage stopper is preferably provided on the dosing member, and a cooperating dosage counter stopper on the drive member. However, this arrangement can essentially also be reversed.

Damage to the spiral dosage stopper cannot be caused by moving the drive member back too forcefully. In particular, the danger of causing damage to the spiral dosage stopper is reduced by the omittance of edges. Furthermore, the spiral dosage stopper makes the manufacture of the preferably injection-molded plastic parts simpler. Dosage can also be made more precise, since a minimum necessary angular spacing between adjacent, discretely determined or determinable rotational angular positions of the dosing member is at best still preferably determined by means provided for determining these rotational angular positions, such means preferably being formed between the dosing member and the casing of the device by locking means of a locking mechanism.

According to the invention, the dosage counter stopper, preferably formed on the drive member, may be of a width which, measured perpendicular to the feed direction, is larger than a distance, measured in the rotational direction, between two immediately consecutive rotational angular positions of the dosing member. In other words, the angle which the dosage counter stopper covers to the spiral dosage stopper may be larger than the angle between two immediately consecutive, determined or determinable rotational angular positions of the dosing member. It is especially preferred that the width of the dosage counter stopper is at least twice the angular spacing between two immediately consecutive rotational angular positions of the dosing member. The dosage counter stopper can be made considerably broader, perpendicular to the feed direction, while still maintaining the same precision and accuracy of dosage as in, for example, the injection device from WO 97/36625. At most, it may be formed running completely around the sliding axis. Preferably, however, its angle of extension does not exceed ten times that of the aforementioned angular spacing.

The drive member and dosing member are preferably arranged such that the one is surrounded by the other. Correspondingly, the two dosage stoppers cooperating during dosage, namely that of the drive member and that of the dosing member, may be provided on the opposing surface areas facing each other on the drive member and dosing member. Preferably, the dosing member concentrically surrounds a distal area of the drive member. In accordance with a preferred example embodiment of this design, the spiral dosage stopper of the dosing member is formed by the proximal front face of the dosing member, and the dosage stopper of the drive member is formed by a dosage cam projecting from the outer surface of the drive member, perpendicular to the feed direction.

BRIEF DESCRIPTION OF THE DRAWINGS

In the following, a preferred example embodiment of the invention will be explained in detail by means of the drawings, in which.

DETAILED DESCRIPTION

Figure 1:
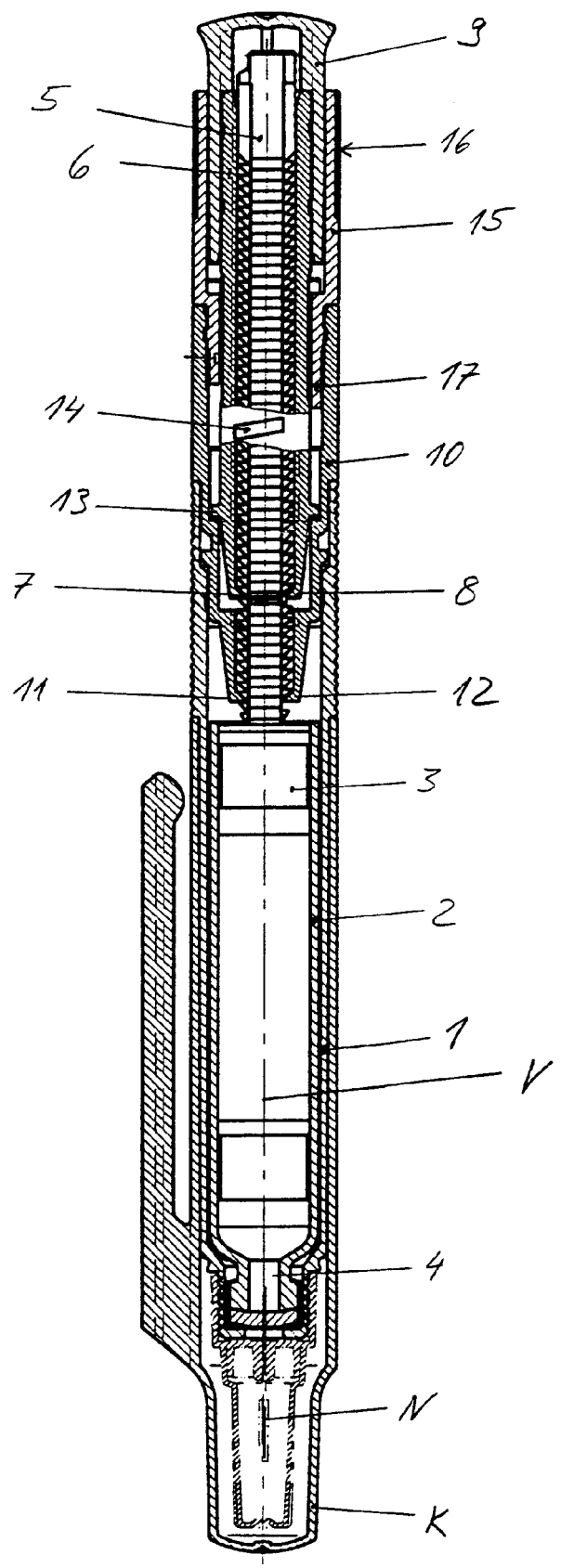
FIG. 1 is a longitudinal sectional view of an injection device, comprising a dosing means in accordance with the invention.
Figure 2:
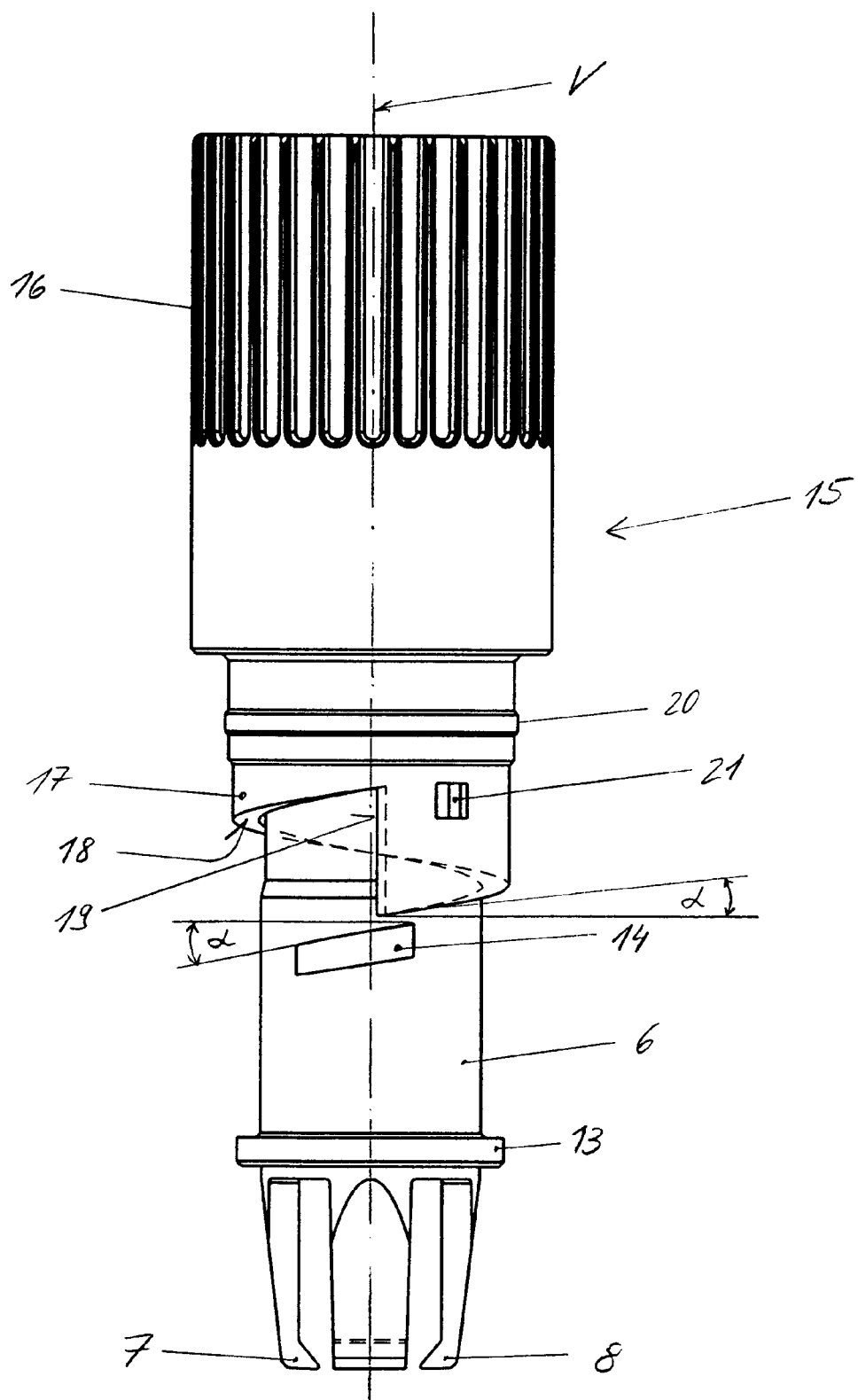
FIG. 2 is a view of a dosing member in accordance with the invention.

FIG. 1 is a longitudinal sectional view of an injection device, in the example embodiment an injection pen. FIG. 2 shows in detail how a drive member 6 and a dosing member 15 are arranged in the injection device.

The injection device comprises a casing with a front casing sleeve 1 and a rear casing sleeve 10 firmly connected to it. The front casing sleeve 1 serves as a receptacle for an ampoule 2. A liquid product in the form of an active ingredient, for example insulin, is contained in the ampoule 2. A piston 3 is also included in the ampoule 2. By moving the piston 3 in the feed direction towards an outlet 4 of the ampoule, the product is forced out of the ampoule 2 through its outlet 4 and delivered through an injection needle N. The front casing sleeve 1 is protected by a cap K. The needle N is further protected by a needle cap.

The piston 3 is moved in the feed direction by a drive means received in the rear casing sleeve 10. The drive means includes a gear rack 5 as a driven member, acting on the piston 3 directly, as well as a drive member 6. The drive member 6 is positioned in the rear casing sleeve 10 and is linearly movable along a sliding axis V in and counter to the feed direction of the piston 3. A lid 9, securely connected to the drive member 6 against sliding or twisting, projects backwards out of the casing.

A dosing member 15 formed as a sleeve body is connected immovably to the rear casing sleeve 10, but is rotatable about the common longitudinal axis which coincides with the sliding axis V. The dosing member 15 projects via a front sleeve portion 17 into the rear casing sleeve 10. Its rear sleeve portion projects out of the rear casing sleeve 10. As may best be seen when FIGS. 1 and 2 are considered together, an annular ring 20 formed on the front sleeve portion 17 and latched into a circumferential groove on the inner surface of the rear casing sleeve 10 serves to immovably fasten the dosing member 15. The rear sleeve portion of the dosing member 15 has a profiled portion 16 to allow the dosing member 15 to be twisted manually without the danger of slipping.

In front of the profiled portion 16, the dosing member 15 has an easily visible dosing scale encircling its outer surface area, which is adjusted to fixed rotational angular positions in which the dosing member 15 locks against the rear casing sleeve 10. The locking mechanism between the dosing member 15 and the rear casing sleeve 10 is formed by elevations 21 on the outer surface of the front sleeve portion 17 of the dosing member 15 and by indentations in the inner surface of the rear casing sleeve 10. The indentations are arranged side by side circumferentially with the same angular spacing and at the same height, on the inner surface of the rear casing sleeve 10. In the fixed rotational angular locking positions of the dosing member 15, the multiple elevations 21 are received precisely into the respectively opposing indentations in the inner surface of the rear casing sleeve 10.

In the fully assembled injection device as shown in FIG. 1, the drive member 6 projects through the dosing member 15. The dosing member 15 concentrically encircles a distal portion of the drive member 6 and also of the driven member 5. The lid 9 projects via a sleeve portion into an annular groove between the drive member 6 and the dosing member 15. The surface portion of the lid 9 projecting out of the dosing member 15 is also provided with a marking, which in cooperation with the marking on the dosing member 15 allows the overall amount of product administered from the ampoule 2 to be exactly determined, even after the dosing member 15 has been fully twisted several times.

Twisting the dosing member 15 sets the maximum dosage path length which the drive member 6 and the gear rack 5 may cover in the feed direction, and thus also the maximum product dosage which may be supplied in one injection. For this purpose, the front sleeve portion 17 of the dosing member 15 is formed as an encircling spiral on the front proximal face 18 of the dosing member 15, i.e. the front sleeve portion 17 progressively falls away with respect to the sliding axis V of the drive member 6, in a circumferential direction from a foremost section of the front face.

Dosage is achieved in a foremost, proximal end position of the drive member 6 in relation to the feed direction, in which a stop cam or boss 13 radially extends from the outer surface area of the drive member 6 and abuts a stopper formed by the rear casing sleeve 10. In this proximal end position of the drive member 6, the dosing member 15 is rotated about the sliding axis V relative to the rear casing sleeve 10 until it reaches the desired dosage position or rotational angular locking position. In this dosage position, a clear dosage space remains between another boss or cam, likewise projecting out of the outer surface area of the drive member 6 and forming a dosage stopper 14, and thus termed dosage cam 14 in the following, and the proximal front face 18 of the dosing member 15 facing said dosage cam 14. Around the dosage space, the drive member 6 may be drawn back, counter to the feed direction, relative to the rear casing sleeve 10 and thus also relative to the piston 3. Withdrawal is achieved manually by pulling the lid 9. The dosage space is equal to the path length of dosage in the subsequent administering.

When the drive member 6 is moved or pulled back, the gear rack 5 remains in its sliding position entered during dosage, relative to the casing. It is secured against movement counter to the feed direction by the blocking means 11 and 12 provided on the rear casing sleeve 10. The blocking means 11 and 12 are locking cams, each formed at a front end of an elastically giving tongue and radially projecting from the tongue inwards towards the gear rack 5. The blocking means 11 and 12 each cooperate with a series of teeth of the gear rack 5 facing them, such that they allow the gear rack 5 to be moved in the feed direction, and prevent movement counter to the feed direction by means of a positive blocking mesh.

The cooperation between the drive member 6 and the dosing member 15 for dosage purposes can best be seen in FIG. 2, which shows the drive member 6 immediately before reaching its distal end position, i.e. the stop position on the dosing member 15. The two cooperating dosage stoppers, namely the proximal, spirally encircling front side 18 of the dosing member 15 and the dosage cam 14 projecting perpendicularly out of the drive member 6, exhibit the same constant pitch or the same constant pitch angle α, relative to the sliding axis V. This gives the spiral dosage stopper 18 its recognizable, continuous course with constant pitch α. A single edge 19 arises, extending parallel to the sliding axis V, and connecting the proximal tip of the dosage stopper 18 to its distal base. The proximal front side 18 of the dosing member 15 exhibits no other edges. The dosage stopper 14 formed by the dosage cam is adapted to the face of the spiral dosage stopper 18, at least on its opposing face facing the spiral dosage stopper 18, such that the dosage cam 14, in the arrangement shown in FIG. 2 comprising the drive and dosing member, can be moved along through a 360° rotation on the dosage stopper 18 as on an inclined plane. The dosage steps of the injection device are exclusively defined by the locking mechanism between the rear casing sleeve 10 and the dosing member 15. The dosage cam of the drive member 6 forming the dosage stopper 14 may be optimally designed with respect to its mechanical strength, independently of the precision of the dosage steps. In the example embodiment, the dosage stopper 14 on the outer surface of the drive member 6 extends over an angle about five times greater than the angular spacing between two immediately consecutive rotational angular locking positions on the dosing member 15.

The gear rack 5 is formed by a cross-sectionally rectangular rod fitted with series of teeth respectively provided on all four sides of a region which is a front region in relation to the feed direction. FIG. 2 shows two series of teeth provided on opposite sides of the gear rack 5 and facing the blocking means 11 and 12. In addition to said two series of teeth, the gear rack 5 further comprises two other series of teeth, provided on opposite side faces of the gear rack 5. The individual teeth of each series of teeth of the gear rack 5 are tapered in the feed direction; in the example embodiment, the flanks of the teeth are simply plane and oblique. The back of each tooth is simply plane, and points perpendicular to the feed direction, and thus to the longitudinal direction of the injection device and of the gear rack 5. The regular spaces between the teeth of the series of teeth are designated 5a. The four series of teeth exhibit the same pitch and are arranged around the gear rack 5 at the same height.

The series of teeth within a pitch are positioned offset to each other in relation to the feed direction.

The blocking means 11 and 12, and two further blocking means cooperating with each of the further series of teeth facing them respectively, are arranged at the same height and at an angular spacing of 90° to each other, with respect to the feed direction. Due to the offset of the series of teeth, only one of the blocking means is ever fully meshing with a tooth gap of the series of teeth facing it, when the gear rack 5 is moved forwards. Opposite each of the other three blocking means are flanks of teeth of the series of teeth facing them, such that these other blocking means can be bent away from the gear rack 5. Accordingly, moving the gear rack 5 in the feed direction causes the blocking means to successively fully mesh with the respective series of teeth facing them; overall, an alternating meshing of the blocking means results. The gear rack 5 is blocked against movement counter to the feed direction by the blocking means being elastically fully latched into or towards an interdental space.

The gear rack 5 is moved in the feed direction by the drive member 6. For this purpose, the drive member 6 tapers off in the feed direction into four tongues, provided at their front ends with locking cams radially projecting inwards. Of the slaving means so formed, the two opposing slaving means 7 and 8 are shown in FIG. 1. In the example embodiment, the slaving means and the blocking means are identical in form and function. Both are formed on elastically giving tongues by locking cams. When the drive member 6 is moved in the feed direction, one of the slaving means presses against the back of one of the teeth of the series of teeth facing it, respectively, such that the gear rack 5 is inevitably slaved in the feed direction. Owing to their elastic give and to the forward sweep of the teeth, the slaving means slide over the series of teeth of the gear rack 5 blocked by the blocking means, when the drive member 6 is moved against the feed direction. As the slaving means taper off into locking cams at the same height in relation to the feed direction, two slaving means never simultaneously fully mesh with one of the regular tooth gaps of the gear rack 5.

FIG. 1 shows the injection device in a starting position, in which the gear rack 5 assumes its rearmost proximal end position relative to the rear casing sleeve 10 and also relative to the drive member 6. In this starting position, the rear half of the casing is supplied by the manufacturer fully assembled with the gear rack 5 and the drive member 6, including the lid 9 and the dosing member 15. The starting position thus corresponds to the storage position of the injection device, in particular of the drive means and the dosing means of the injection device. In the example embodiment, the injection device is a disposable pen. Reusability, i.e. replacing the ampoules, may however be made possible by simple modifications.

In the starting position of the injection device, with an inserted ampoule 2, the product dosage to be administered in the first injection is set by the user. To this end, the dosing member 15 is twisted into a given dosage position corresponding to the desired product dosage. In this dosage position, the dosage cam 14 of the drive member 6 and the dosage stopper 18 facing it, formed by the proximal front face of the dosing member 15, form the clear dosage space. In the starting position, only the blocking means 11 abuts the back of a tooth of the gear rack 5. Although the other blocking means are pre-latched towards the gear rack 5 up to their disengaged neutral positions, in the starting position they are positioned in tooth gaps which are elongated compared to the regular tooth gaps. Of the slaving means, only the slaving means 7 abuts the back of a tooth in the starting position. The other slaving means are disengaged in their neutral positions in the tooth gaps facing them in the starting position, i.e. they are not bent away in the starting position. The series of teeth of the gear rack 5 each exhibit a tooth in front of their elongated tooth gaps by the blocking means. The teeth which define the elongated tooth gaps in the feed direction are only used for functional tests of the injection device. As soon as the device is assembled, the gear rack 5 is pushed through the blocking means arranged concentrically to it, up to the starting position indicated.

Pulling the lid 9 retracts the drive member 6 counter to the feed direction, from its proximal end position with respect to the rear casing sleeve 10 up to its distal end position. When the drive member 6 is retracted, its slaving means slide over the series of teeth of the gear rack 5 facing them, the blocking means 11 preventing it from being slaved.

During injection, the drive member 6, and thus also the gear rack 5, are moved along the dosage path length in the feed direction by pushing against the lid 9. The gear rack 5 thereby pushes the piston 3 in the ampoule 2 towards the outlet 4, and product is delivered.

In the example embodiment, the slaving means of the drive member 6 are arranged behind the blocking means with respect to the feed direction. The concentric arrangement of the blocking means and the tongue is such that they may be radially bent outwards against their inherent elastic restoring force, away from the gear rack 5, in correspondence with the shape of the teeth of the series of teeth of the gear rack 5. In the example embodiment, both the blocking means and the slaving means are each arranged among themselves at the same height with respect to the feed direction, while the series of teeth of the gear rack 5 exhibit an offset with respect to each other, such that the regular tooth gaps of the series of teeth are at various heights with respect to the feed direction. This has the effect that there is never more than one blocking means or slaving means fully meshed with one of the regular tooth gaps at a time. Instead of this arrangement, the blocking means and the slaving means may also be correspondingly offset with respect to the feed direction at various heights, and the series of teeth of the gear rack 5 arranged at the same height. The arrangement chosen in the example embodiment is, however, advantageous for manufacture.

In the starting position shown in the Figures, which in particular for the parts of the injection device arranged in the rear casing sleeve 10, namely the gear rack 5, the drive member 6 and the blocking means, is also the storage position, the danger of material fatigue would exist for the blocking means and slaving means which cannot latch into tooth gaps in the starting position, such that they could be at least partially or, as in the embodiment completely, disengaged, for these blocking means and slaving means would be bent away in the starting position. In this bent away position, the slaving means and blocking means are elastically biased. If this state is maintained for longer periods of time, it cannot be guaranteed with the required certainty that they will elastically bend back into their functional position, namely the position abutting the back of a tooth.

The gear rack 5, however, comprises elongated tooth gaps where the blocking means and slaving means which do not abut the backs of teeth of the gear rack 5 in the starting position mesh in the starting position of the injection device,.

In the starting position, the blocking means 11 blocks the gear rack 5 from moving counter to the feed direction. In this starting position, the product dosage to be administered by the next injection is first selected using the dosing member 15. Then, the drive member 6 is retracted by the dosage space corresponding to this dosage. In this action, the slaving means slide over the teeth of the series of teeth of the gear rack 5 facing each of them, the offset of the series of teeth ensuring that the slaving means successively latch in regular exchange, such that a number of locking procedures occur for each single slaving means within a pitch. In the distal end position of the drive member 6 determined by the dosing member 15, the latching of at least one slaving means may be guaranteed with much greater certainty than would be the case with just one series of teeth and one slaving means. The same correspondingly applies to the cooperation between the series of teeth and the blocking means. When the drive member 6 is moved counter to the feed direction, and when the gear rack 5 is moved in the feed direction, one of the slaving means and one of the blocking means each fully mesh in turn, and thus undergo slaving or blocking mesh, each latching into an elongated tooth gap, in the starting position.

In the foregoing description a preferred embodiment of the invention has been presented for the purpose of illustration and description. It is not intended to be exhaustive or to limit the invention to the precise form disclosed. Obvious modifications or variations are possible in light of the above teachings. The embodiment was chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A device for administering an injectable product in doses, comprising:
   a) a casing, comprising a reservoir for said product;
   b) a piston, forcing product out of said reservoir when moved in a feed direction towards a reservoir outlet;
   c) a drive member, which may be moved along a sliding axis in said feed direction up to a proximal end position, and counter to said feed direction up to a distal end position;
   d) a driven member, which is prevented from moving counter to said feed direction, and is slaved by said drive member when said drive member is moved in said feed direction, so moving said piston in said feed direction;
   e) a dosing member, which may be rotated about said sliding axis of said drive member, to set the product dosage to be administered;
   f) wherein in said distal end position, said drive member and said dosing member abut via at least one dosage stopper each, one of which is provided on said drive member and the other on said dosing member; and wherein
   g) at least one of said dosage stoppers at least partially encircles said sliding axis of said drive member in the form of a spiral exhibiting a continuous course with a constant pitch.

2. The device as set forth in claim 1, characterized in that said dosing member can be twisted between determined or determinable rotational angular positions, preferably by being locked into rotational angular locking positions, and in the said other dosage stopper, preferably provided on said drive member, extends to said spiral dosage stopper, preferably provide on said dosing member, covering an angle larger than an angular spacing between immediately consecutive rotational angular positions of said dosing member.

3. The device as set forth in claim 2, wherein the other dosage stopper extends over an angle which is at least twice said angular spacing between immediately consecutive rotational angular positions of said dosing member.

4. The device as set forth in claim 2, characterized in that said second dosage stopper extends over an angle at most ten times said angular spacing between immediately consecutive rotational angular positions of said dosing member.

5. The device as set forth in claim 1, characterized in that said other dosage stopper preferably provided on said drive member is of the same pitch as said spiral dosage stopper, with respect to said spiral dosage stopper preferably provided on said doing member.

6. The device as set forth in claim 5, wherein said spiral dosage stopper is provided on a proximal front face of said dosing member and the other dosage counter stopper is provided by means of a cam projecting out of said drive member perpendicular to said feed direction.

7. A device for administering an injectable product in doses, comprising:
   a) a casing comprising a reservoir for said product, said reservoir having a reservoir outlet;
   b) a piston for forcing product out of said reservoir when moved in a feed direction towards the reservoir outlet;
   c) a drive member which may be moved axially in the feed direction to a proximal end position and generally opposite to the feed direction to a distal end position;
   d) a driven member which is driven in the feed direction by said drive member when said drive member is moved in the feed direction, thereby moving said piston in the feed direction;
   e) a dosing member which may be rotated about the drive member to set the product dosage to be administered;
   f) wherein, in said distal end position, said drive member and said dosing member abut via complementary elements, one of said elements comprising a spiral having a continuous course.

8. The device as set forth in claim 7, wherein said spiral has a substantially constant pitch.

9. The device as set forth in claim 7, wherein said spiral is formed by a face of the dosing member.

10. The device as set forth in claim 9, wherein the other of said complementary elements comprises a cam projecting from the drive member.

11. The device as set forth in claim 10, wherein the cam is generally perpendicular to the feed direction.

12. The device as set forth in claim 7, wherein the complementary elements comprise dosage stoppers, one of which is associated with the drive member and the other of which is associated with the dosing member.

13. The device as set forth in claim 12, wherein the dosage stopper associated with the dosing member is the spiral, wherein the dosing member is movable among rotational angular positions, and wherein the dosage stopper associated with the drive member extends to the spiral covering an angle larger that an angular spacing between immediately consecutive rotational angular positions of the dosing member.

14. The device as set forth in claim 13, wherein the dosage stopper associated with the drive member extends over an angle which is at least twice said angular spacing between immediately consecutive rotational angular positions of said dosing member.

15. The device as set forth in claim 12, wherein the dosage stopper associated with the drive member extends over an angle which is at most ten times said angular spacing between immediately consecutive rotational angular positions of said dosing member.

16. The device as set forth in claim 8, wherein the other complementary element has substantially the same pitch as the spiral.

17. A device for administering an injectable product in doses, comprising:
   a casing comprising a reservoir for said product, said reservoir having a reservoir outlet;
   a piston for forcing product out of said reservoir when moved in a feed direction towards the reservoir outlet;
   a drive member which may be moved axially in the feed direction to a proximal end position and generally opposite to the feed direction to a distal end position;
   a driven member which is driven in the feed direction by said drive member when said drive member is moved in the feed direction, thereby moving said piston in the feed direction; and
   a dosing member which may be rotated about the drive member to set the product dosage to be administered, wherein, in said distal end position, said drive member and said dosing member abut via complementary dosage stoppers, one of said dosage stoppers comprising a spiral associated with the dosing member and having a continuous course and a substantially constant pitch and the other dosage stopper comprising a cam projecting from the drive member.

* * * * *